United States Patent [19]

Quinlan

[11] 4,418,195
[45] Nov. 29, 1983

[54] SILICON-CONTAINING QUATERNARY AMMONIUM THIAZINES

[75] Inventor: Patrick M. Quinlan, Webster Groves, Mo.

[73] Assignee: Petrolite Corporation, St. Louis, Mo.

[21] Appl. No.: 814,513

[22] Filed: Jul. 11, 1977

[51] Int. Cl.³ .................... C07F 7/18; A61K 31/695
[52] U.S. Cl. ........................... 544/58.2; 544/59; 544/60; 424/246; 252/389 R; 252/389 A
[58] Field of Search .............................. 544/59, 58, 60

[56] References Cited

U.S. PATENT DOCUMENTS

| | | | |
|---|---|---|---|
| 3,801,572 | 4/1974 | Berger | 260/243 R |
| 3,828,036 | 8/1974 | Quinlan | 260/243 B |
| 4,113,709 | 9/1978 | Quinlan | 544/60 |
| 4,276,416 | 6/1981 | Quinlan | 544/58.2 |

*Primary Examiner*—Mark L. Berch
*Attorney, Agent, or Firm*—Sidney B. Ring; Hyman F. Glass; Leon J. Bercovitz

[57] ABSTRACT

This invention relates to silicon-containing thiazines and to the process of preparing them. These are illustrated by the following formulae:

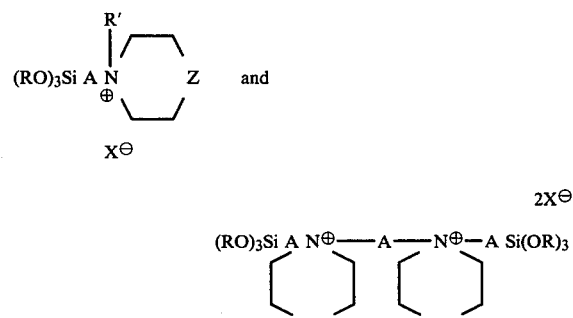

where
R and R' are substituted groups, for example hydrocarbon groups such as alkyl, aryl, cycloalkyl, etc.; A is alkylene, Z is a sulfur-containing group such as S, SO, SO₂ and X is an anion.

These compositions have a wide variety of uses including their use as corrosion inhibitors, microbiocides, etc.

5 Claims, No Drawings

SILICON-CONTAINING QUATERNARY AMMONIUM THIAZINES

My inventions relating to quaternary thiazines have been disclosed and claimed in the following:
U.S. Pat. No. 3,770,732
U.S. Pat. No. 3,828,036

I have now discovered a new class of quaternary thiazines which is silicon-containing.

These compounds are prepared by reacting a silicon containing at least one amino group having one nitrogen-bonded hydrogen with a divinyl sulfur compound. Where the silicon-containing amine has one secondary amino group a monoquaternary is formed and where it has 2 secondary amino groups a diquaternary compound is formed.

These are prepared by reacting an acid salt of the silicon-containing amine with the divinyl sulfur compound according to the following equation:

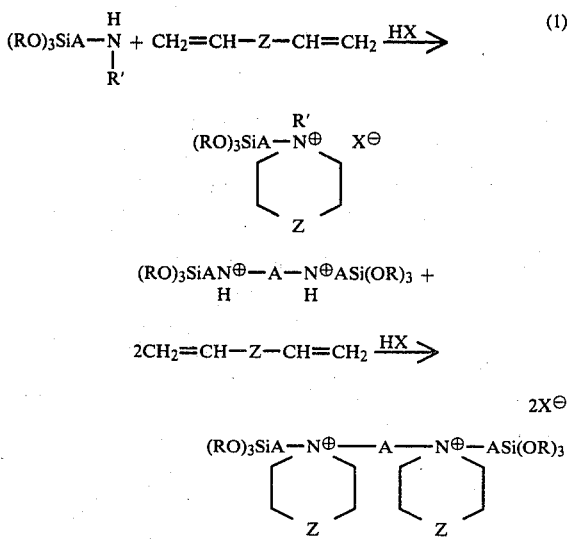

where R is a substituted group such as hydrocarbon for example alkyl, aryl, aralkyl, cycloalkyl, etc.

A is alkylene, Z is S, SO, $SO_2$ and X is an anion, for example an inorganic anion, such as halide, sulfate, phosphate, nitrate, perchlorate, etc., or an organic containing acid such as an organic sulfonate, phosphonate, etc., such as alkyl, cycloalkyl, alkaryl, aryl, aralkyl, sulfonate, etc.

In the preferred embodiment, R and R' are lower (i.e., less than 7 carbons) alkyl, and A is lower alkylene, and X is a halide.

Examples of divinyl sulfur compounds are

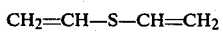

$CH_2=CH-S-CH=CH_2$ $CH_2=CH-SO-CH=CH_2$ $CH_2=CH-SO_2-CH=CH_2$

Suitable acids that may be employed herein are hydrohalic acids such as hydrochloric, hydrobromic, hydroiodic, etc.; sulfuric, phosphoric, nitric, perchloric, hydrocarbon sulfonic acids such as methanesulfonic, ethyl sulfonic, benzyl sulfonic and the like.

In carrying out the reaction it is preferred to form the amine salt in situ, that is in a solvent such as ethanol in which it is soluble. However, if desired, the salt may first be isolated and purified. To the solution of the amine salt in a suitable inert solvent is added the divinyl sulfone. The preferred temperature is about 20° to 50° C. though higher or lower temperatures may be employed. A catalyst such as triethylamine may be used. In most instances the thiazine dioxide quaternary nitrogen salt precipitates from the alcoholic medium and is purified by recrystallization. In some cases it is necessary to reduce the final volume in order to isolate the desired product.

The preferred class of silicon-containing amines are of the general formula

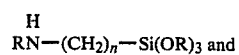

$RN-(CH_2)_n-Si(OR)_3$ and

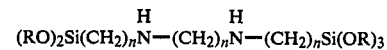

where
R is alkyl, preferably lower alkyl, i.e., methyl, ethyl, propyl, etc.:
n is a number such as 2–10 or greater, for example 2–6, but preferably 2–3.

The following are illustrative examples of silicon compounds convertible to quaternary thiazines.

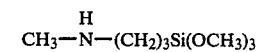

$CH_3-N-(CH_2)_3Si(OCH_3)_3$

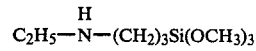

$C_2H_5-N-(CH_2)_3Si(OCH_3)_3$ $C_3H_7-N-(CH_2)_3Si(OCH_3)_3$

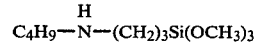

$C_4H_9-N-(CH_2)_3Si(OCH_3)_3$

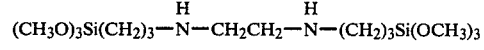

$(CH_3O)_3Si(CH_2)_3-N-CH_2CH_2-N-(CH_2)_3Si(OCH_3)_3$

$(C_2H_5O)_3Si(CH_2)_3-N-CH_2CH_2-N-(CH_2)_3Si(OC_2H_5)_3$ $(C_3H_7O)_3Si(CH_2)_3N-CH_2CH_2-N(CH_2)_3Si(OC_3H_7)_3$

The following examples are presented for purposes of illustration and not of limitation.

EXAMPLE 1

Divinyl sulfone 29.5 g (0.25 mole) was slowly added to a solution of 48.3 g (0.25 mole) (Trimethoxysilyl propyl) methyl amine in 125 ml. of 4 N ethanolic hydrochloric acid. The reaction mixture became warm. After 24 hours crystals had appeared in the reaction mixture. The colorless crystalline product was filtered and washed several times with cold ethanol. It was recrystallized from aqueous ethanol. The product had the following structure:

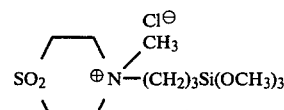

Analysis: calc. for C$_{11}$H$_{26}$ Cl Si NO$_5$S(%): N, 4.03; Cl, 10.21. Found (%) N, 4.10; Cl, 10.15.

EXAMPLE 2

Divinyl sulfone 29.5 g (0.25 mole) was slowly added to a solution of 51.8 g (0.25 mole) of (Trimethoxysilyl propyl) ethyl amine in 125 ml. of 4 N ethanolic hydrochloric acid. The product was isolated and purified as before. It had the following structure:

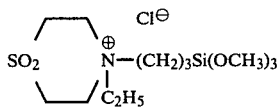

Analysis: Calc. for C$_{12}$H$_{28}$ Cl Si NO$_5$S(%); N, 3.87; Cl, 9.81. Found (%) N, 3.92; Cl, 9.72.

EXAMPLE 3

Divinyl sulfone 29.5 g (0.25 mole) was slowly added to a solution of 55.3 g (0.25 mole) (Trimethoxysilyl propyl) propyl amine in 100 ml. of ethanol that had been acidified with hydrobromic acid. The product was isolated and purified as before. The crystalline product had the following structure:

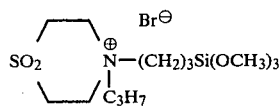

EXAMPLE 4

In a similar manner Divinyl sulfone 29.5 g (0.25 mole) was reacted with 48.3 g (0.25 mole) of (Trimethoxysilyl propyl) methyl amine in ethanolic hydroiodic acid. The product had the following structure:

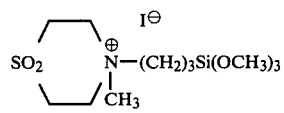

EXAMPLE 5

Divinyl sulfone 29.5 g (0.25 mole) was slowly added to a solution of 43.79 g (0.125 mole) bis(trimethoxysilyl propyl) ethylenediamine in 125 ml. of 4 N ethanolic hydrochloric acid. The reaction mixture became warm and crystals appeared upon cooling. The crystalline product was filtered and washed with cold ethanol. It had the following structure:

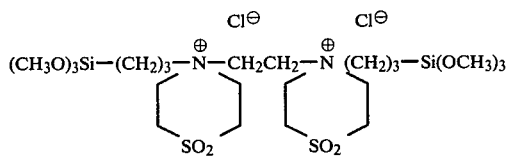

Anal., Calc. for C$_{22}$H$_{50}$ N$_2$O$_{10}$ Si$_2$ S$_2$ Cl$_2$ (%); N, 4.04; Cl, 10.24. Found (%) N, 3.71; Cl, 9.65.

EXAMPLE 6

In a similar manner divinyl sulfone 29.5 g (0.25 mole) was reacted with 58.5 g (0.125 mole) of bis(triethoxysilyl propyl) ethylenediamine in ethanolic hydrogen bromide. The product had the following structure:

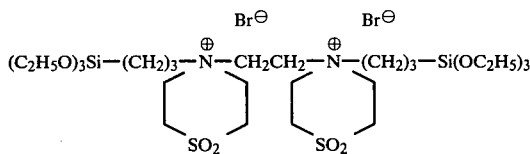

EXAMPLE 7

In a similar manner divinyl sulfone 29.5 g (0.25 mole) was reacted with 69.0 g (0.125 mole) of bis(tripropoxysilyl propyl) ethylenediamine in ethanolic hydrogen iodide. The product had the following structure:

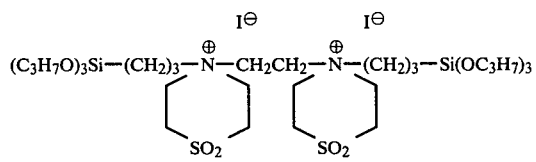

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas wells which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formation and/or substantial quantities of oil can no longer be obtained by the usual pumping methods, various processes are sometimes used for the treatment of the oil-bearing formation in order to increase the flow of the oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system." If the water is recirculated in a closed system without substantial aeration, the secondary recovery method is referred to herein as a "closed water flooding system."

Because of the corrosive nature of oil field brines, to economically produce oil by water flooding, it is necessary to prevent or reduce corrosion since corrosion increases the cost thereof by making it necessary to repair and replace such equipment at frequent intervals.

I have now discovered a method of preventing corrosion in systems containing a corrosive aqueous media, and most particularly in systems containing brines, which is characterized by employing the compositions of this invention.

I have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compositions of this invention can also be used in such water disposal walls thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of the reducing compound, sufficient to prevent corrosion, in concentrations of about 10 p.p.m. to 10,000 p.p.m., or more, for example, about 50 to 5,000 p.p.m., but preferably about 15 to 1,500 p.p.m. The upper limiting amount of the compounds is determined by economic considerations. Since the success of a water flooding operation manifestly depends upon its total cost being less than the value of the additional oil recovered from the oil reservoir, it is quite important to use as little as possible of these compounds consistent with optimum corrosion inhibition. Optimum performance is generally obtained employing about 100 p.p.m. Since these compounds are themselves inexpensive and are used in low concentrations, they enhance the success of a flood operation by lowering the cost thereof.

In addition, these compounds are not sensitive to oxygen content of the water and these are effective corrosion inhibitors in both open water flooding systems and closed water flooding systems.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc., and in conjunction with other secondary recovery methods.

USE IN FLUIDS FOR DRILLING WELLS

This phase of the invention relates to the use of the compounds of this invention as corrosion inhibitors in producing an improved drilling fluid useful in drilling oil and gas wells.

Fluids commonly used for the drilling of oil and gas wells are of two general types: water-base drilling fluids comprising, for example, a clay suspended in water, and oil-base drilling fluids comprising, for example, a clay or calcium carbonate suspended in mineral oil.

A third type of drilling fluid which has recently been developed, is one of oil-in-water or water-in-oil emulsion, for example, emulsions of mineral oil in water or water in mineral oil formed by means of emulsifiers such as sulfuric acid; Turkey-red oil; soaps of fatty acids, for example sodium oleate; emulsoid colloids, for example starch, sodium alginate, etc. Varying amounts of finely divided clay, silica, calcium carbonate, blown asphalt, and other materials may be added to these emulsions to improve their properties and control their weight.

I have now discovered that the compositions of this invention can be employed as a corrosion inhibitor in drilling fluids.

USE IN AIR DRILLING

It has long been conventional practice in drilling deep bore holes to circulate a drilling mud down through the drill stem and up through the bore hole between the wall of the bore hole and the drill stem for the removal of chips or cuttings from the bore hole and to provide support for the wall of the bore hole. More recently, in the drilling of holes in which wall support provided by drilling mud is not employed, drilling has been carried out with the use of air for chip removal. Such drilling is not only normally faster than mud drilling but is indispensable in areas where the supply of water is limited or when drilling through cavernous formations into which the drilling mud flows and becomes lost.

The increasing popularity of air or gas drilling has come about not only because this method of drilling is frequently faster, as noted above, but for the additional reasons that the drill bits last longer, the provision and handling of water under wide ranges of temperature conditions is avoided, boring samples are easily observed when they are not mixed with mud, and there is no loss involved as in the case of mud drilling when drilling through cavernous formations. Furthermore, prompt removal of water entering the hole maintains a dry hold and the likelihood of wall collapse is thereby reduced.

In a typical air drilling operation there may be provided, for example, an up-flow of air in the bore hold having a velocity of the order of 3,000 feet per minute. This flow of air upwardly through the bore hole, which is produced by air pumped downwardly through the drill stem, provides adequate removal of cuttings. The air is delivered to the drill stem at pressures of 20 to 60 lbs. per square inch and for dewatering or for breaking obstructions, as will be hereinafter described, the pressures may be increased to 180 to 200 lbs. or more per square inch.

Air drilling operations are frequently hampered by the inflow of water into the bore hole when the drill bit is penetrating a water bearing stratum or when the bore hole has passed through a water bearing stratum that has not been cased. Normally, if drilling proceeds uninterruptedly both before and during penetration into a water bearing stratum, the flow of air is sufficient to blow the water out of the bore hole along with the cuttings and drilling dirt. There are, however, two major problems encountered in air drilling when water is entering the bore hole. The first problem occurs when there is a small inflow of water sufficient to cause a dampening of the cuttings which, under certain conditions, will then ball up, clogging and sometimes jamming the drill bit. The second problem is encountered when there is a substantial amount of water remaining in the bottom of the bore hole during drilling causing a sloughing of the side wall of the bore hole. This latter condition may arise even though the water entering the bore hole is being blown out of the hole as fast as it enters. If there is a substantial inflow of water or if there is a substantial flow of water past a region of the bore hole susceptible to this condition, the water passing that region of the bore hole may cause a sloughing of the side wall.

The addition of foam forming materials to the air flow when air drilling is employed in conjunction with sufficient water to provide foaming gives rise to numerous advantages in drilling operations. The water may be introduced either through a water bearing stratum being penetrated by the drill bit or, alternatively, if the hole is dry, water may be introduced from the surface of the earth through the drill stem in conjunction with the delivery of compressed air and foam forming material through the drill stem to the drill bit. In either case the water may be said to be existing in the bore hole, and drilling operations are described in U.S. Pat. No. 3,130,798.

The compositions of this invention can be employed as a corrosion inhibitor in a drilling system.

The compositions of this invention may also be added to other aqueous and/or oxygenated systems such as steam generating systems, water circulating systems such as in cooling towers, in automobile radiators, in diesel locomotive engines, in boiler water, etc.

The amount of the compositions of the invention to be employed as a corrosion inhibitor can vary widely depending upon particular compounds, the particular system, the amounts of oxygen present, etc. I may employ concentrations of from about 0.5 to 5,000 p.p.m., such as from about 4 to 4,000 p.p.m., for example from about 20 to 2,000 p.p.m., but preferably from about 100 to 1,000 p.p.m. The optimum amount, to be determined in each instance, which will depend on function and economics, can be lesser or greater than the above amounts under proper conditions.

Corrosion tests were made using sand blasted 1020 mild steel coupons monitored by polarization resistance meter, a PAIR instrument described in U.S. Pat. No. 3,406,101. These tests were made in cylindrical containers of 1,500 cc volume with provision for constant stirring by means of a motor driven impeller. A thermostatically controlled immersion heater maintained an average temperature of 80° C. and an air inlet kept the fluids constantly saturated with air. Between each test the cylinder was cleaned with steam, benzene, acetone and thoroughly washed with clean water. Results of these corrosion tests made in various aqueous environments is shown in the following Table.

Protection is calculated in the usual manner from corrosion rate ($R_1$) of fluids without inhibitor and corrosion rate ($R_2$) in presence of particular inhibitor according to the formula $$(R_1 - R_2/R_1) \times 100 = \text{Percent protection.}$$

TABLE A

Corrosion results in Laboratory brine
(4.2% NaCl, 1.7% Mg $Cl_2$, 0.15 $CaCl_2$, 0.09% $Na_2SO_4$ pH 6.0)
Air Saturated Brine at 80° C.

| Compound | Concentrations | Corrosion Rate (mpy) | % Protection |
|---|---|---|---|
| Example 1 | 1000 ppm | 2.5 | 98% |
| Example 1 | 125 ppm | 6.3 | 91% |
| Example 2 | 1000 ppm | 2.6 | 96% |
| Example 2 | 125 ppm | 5.5 | 93% |
| Example 5 | 1000 ppm | 1.8 | 99% |
| Example 6 | 1000 ppm | 2.5 | 97% |
| Blank | — | 78.0 | — |

USE AS A MICROBIOCIDE

(I) In water treatment

This phase of the present invention relates to the treatment of water. More particularly, it is directed to providing improved means for controlling microbiological organisms including bacteria, fungi, algae, protozoa, and the like, present in water.

It is well known that ordinary water contains various bacteria, fungi, algae, protozoa and other microbiological organisms which, if uncontrolled, multiply under certain conditions so as to present many serious problems. For example, in swimming pools the growth of these microbiological organisms is very undesirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, as well as many other costly and deleterious effects.

In other industrial applications where water is used in processes, as for example, as a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplied, in cooling towers, air conditioning systems, on the farm and ranch, in the factory, in civilian and military hospitals and dispensaries, in camps, for swimming pools, baths and aquaria, waterworks, wells, reservoirs, by fire-fighting agencies, on maritime and naval vessels, in boilers, steam-generators and locomotives, in pulp and paper mills, for irrigation and drainage, for sewage and waste disposal, in the textile industry, in the chemical industries, in the tanning industry, et cetera, and which will render said water supplies bactericidal, fungicical and algicidal. They further provide a simple process whereby water supplies, for whatever purposes intended, are rendered bacteriostatic, fungistatic and algistatic, i.e., said water supplies treated by the process of this invention will resist and inhibit the further growth or proliferation of bacteria, fungi, algae and all forms of microbial life therein.

(II) Water flooding in secondary recovery of oil

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding taking place in the presence of sulfate-reducing bacterial.

Water flooding is widely used in the petroleum industry to effect secondary recovery of oil. By employing this process the yield of oil from a given field may be increased beyond the 20-30 percent of the oil in a producing formation that is usually recovered in the primary process. In flooding operation, water is forced under pressure through injection wells into or under oil-bearing formations to displace the oil therefrom to adjacent producing wells. The oil-water mixture is usually pumped from the producing wells into a receiving tank where the water, separated from the oil, is siphoned off, and the oil then transferred to storage tanks. It is desirable in carrying out this process to maintain a high rate of water injection with a minimum expenditure of energy. Any impediment to the free entry of water into oil bearing formations seriously reduces the efficiency of the recovery operation.

The term "flood water" as herein employed is any water injected into oil bearing formations for the secondary recovery of oil. In conventional operations, the water employed varies from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and/or existing in sufficiently high numbers to constitute an appreciable mass, thereby plugging the pores of the oil-bearing formation. Free-plugging increases the pressure necessary to drive a given volume of water into an oil-bearing formation and oftentimes causes the flooding water to by-pass the formation to be flooded. In addition, microorganisms may bring about corrosion by acting on the metal structures of the wells involved, producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

(III) Hydrocarbon treatment

This phase of the present invention relates to the use of these compounds as biocides in hydrocarbon systems.

In addition to being used as biocides in aqueous systems, the compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product; that microorganisms cause the formation of gums, $H_2S$, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

The compositions of this invention can be employed in hydrocarbon systems.

MICROBIOCIDAL TESTING

The screening procedure was as follows: a one percent by weight solution of the test compound in water was prepared. The solution was aseptically added to a sterile broth that would support the growth of the test organism, *Desulfovibro desulfuricans*, to provide a concentration of 50 and 100 parts by weight of test compound per million parts by weight of broth. A general growth medium, such as prescribed by the American Petroleum Institute was used. The broth containing the test compound then was dispersed in 5 cc. amounts into sterile disposable tubes and the tubes were inoculated with the growing test organism and incubated at 35° C. for 24 hours. The absence or presence of growth of the microorganisms was determined by visual inspection by an experienced observer.

Following is a summary of the results of the testing of examples of this invention.

| Compound example number | Concentration of test compound, p.p.m. | Results |
| --- | --- | --- |
| Ex. 1 | 50 | Gave control.[1] |
| Ex. 3 | 50 | Gave control.[1] |
| Ex. 5 | 50 | Gave control.[1] |
| Ex. 7 | 50 | Gave control.[1] |

[1] By control is meant that the test compound was biostatic or biocidal—i.e., no growth of the test organism occurred under the test conditions.

I claim:

1. A compound of the formula

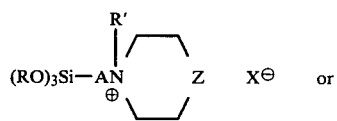

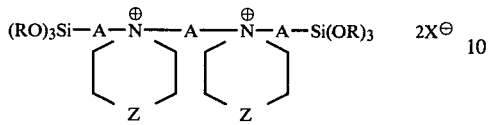

where
- R and R' are alkyl, aryl, aralkyl and cycloalkyl;
- Z is S, SO, SO$_2$;
- A is alkylene; and
- X is an anion.

2. A compound of claim 1 where R and R' are alkyl; Z is SO$_2$; and X is an anion.

3. A compound of claim 2 where R and R' are lower alkyl, A is lower alkylene and X is a halide.

4. A compound of claim 3 where R and R' are methyl, ethyl, or propyl, and A is $-(CH_2)_{2-3}-$.

5. A compound of claim 4 of the formula

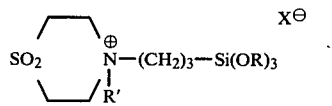

where R and R' are ethyl, methyl, or propyl or

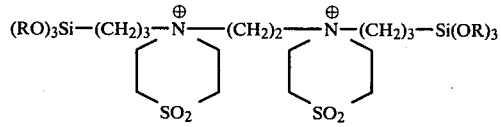

where R is ethyl, methyl, or propyl.

* * * * *